(12) United States Patent
Hu et al.

(10) Patent No.: US 11,759,532 B2
(45) Date of Patent: Sep. 19, 2023

(54) MRNA TARGETING MOLECULE COMPRISING N-ACETYLGALACTOSAMINE BINDING POLYPEPTIDE AND PREPARATION METHOD THEREFOR

(71) Applicant: Shenzhen Rhegen Biotechnology Co., Ltd., Shenzhen (CN)

(72) Inventors: Yong Hu, Shenzhen (CN); Miaomiao Zhang, Shenzhen (CN)

(73) Assignee: ShenZhen Rhegen Biotechnology Co., Ltd., Shenzhen (CN)

(*) Notice: Subject to any disclaimer, the term of this patent is extended or adjusted under 35 U.S.C. 154(b) by 0 days.

(21) Appl. No.: 17/693,173

(22) Filed: Mar. 11, 2022

(65) Prior Publication Data

US 2022/0265859 A1  Aug. 25, 2022

Related U.S. Application Data

(63) Continuation of application No. PCT/CN2020/136010, filed on Dec. 14, 2020.

(30) Foreign Application Priority Data

Dec. 17, 2019 (CN) .......................... 201911300610.2

(51) Int. Cl.
*A61K 47/64* (2017.01)
*A61K 47/65* (2017.01)
(Continued)

(52) U.S. Cl.
CPC ........ *A61K 48/0058* (2013.01); *A61K 47/549* (2017.08); *A61K 47/64* (2017.08);
(Continued)

(58) Field of Classification Search
None
See application file for complete search history.

(56) References Cited

U.S. PATENT DOCUMENTS 6,537,749 B2  3/2003 Kuimelis et al.
8,106,022 B2  1/2012 Manoharan et al.
(Continued)

FOREIGN PATENT DOCUMENTS

CN  1297907 A  6/2001
CN  1347903 A  5/2002
(Continued)

OTHER PUBLICATIONS

Stefanescu et al., Epitope Structure of the Carbohydrate Recognition Domain of Asialoglycoprotein Receptor to a Monoclonal Antibody Revealed by High-Resolution Proteolytic Excision Mass Spectrometry. Journal of The American Society for Mass Spectrometry. vol. 22, pp. 148-157 (2011) (Year: 2011).*
(Continued)

*Primary Examiner* — Arthur S Leonard
(74) *Attorney, Agent, or Firm* — Wilson Sonsini Goodrich & Rosati

(57) ABSTRACT

Disclosed herein are an mRNA targeting molecule comprising an N-acetylgalactosamine binding polypeptide and a preparation method therefor. A plasmid vector containing a DNA fragment formed by sequentially connecting a promoter, a target gene, a specific protease cleavage sequence, and a polynucleotide sequence encoding a GBD capable of binding to N-acetylgalactosamine, is transcribed to obtain an mRNA, which is connected to a DNA-puromycin linker under the action of a T4 ligase. The resulting connection product is subjected to protein translation, followed by cleavage using a specific protease to obtain an mRNA-puromycin-GBD complex, which then binds to a GBD protein sequence under the action of an N-acetylgalactosamine transferase to form an mRNA-puromycin-GBD-GalNAc complex, thereby modifying the mRNA with GalNAc, thus achieving the purpose of precise administration in
(Continued)

a process of mRNA drug delivery and increasing the efficacy of the mRNA drug molecule.

23 Claims, 5 Drawing Sheets

Specification includes a Sequence Listing.

(51) Int. Cl.
A61K 47/54 (2017.01)
A61K 48/00 (2006.01)
A61P 1/16 (2006.01)
C12N 15/87 (2006.01)

(52) U.S. Cl.
CPC .......... *A61K 47/65* (2017.08); *A61K 48/0033* (2013.01); *A61P 1/16* (2018.01); *C12N 15/87* (2013.01)

(56) References Cited

U.S. PATENT DOCUMENTS

| | | | |
|---|---|---|---|
| 8,828,956 | B2 | 9/2014 | Manoharan et al. |
| 9,271,996 | B2 | 3/2016 | De et al. |
| 9,295,689 | B2 | 3/2016 | De et al. |
| 9,506,030 | B2 | 11/2016 | Bhat |
| 9,512,456 | B2 | 12/2016 | Wang et al. |
| 9,867,882 | B2 | 1/2018 | Manoharan et al. |
| 10,155,029 | B2 | 12/2018 | Chakraborty et al. |
| 10,806,791 | B2 | 10/2020 | Manoharan et al. |
| 10,844,379 | B2 | 11/2020 | Prakash et al. |
| 2010/0055761 | A1 | 3/2010 | Seed et al. |
| 2011/0124520 | A1 | 5/2011 | Love et al. |
| 2013/0022538 | A1 | 1/2013 | Rossi et al. |
| 2016/0209421 | A1 | 7/2016 | Suga |
| 2019/0085331 | A1 | 3/2019 | Hadwiger et al. |
| 2019/0160176 | A1 | 5/2019 | Heyes et al. |
| 2019/0343933 | A1 | 11/2019 | Horscroft et al. |
| 2020/0085944 | A1 | 3/2020 | Heidenreich et al. |
| 2021/0017214 | A1 | 1/2021 | Albaek et al. |
| 2021/0054018 | A1* | 2/2021 | Murray .................. C12P 19/30 |
| 2022/0090055 | A1* | 3/2022 | Krauss ................. A61K 47/646 |
| 2022/0118099 | A1 | 4/2022 | Hu et al. |

FOREIGN PATENT DOCUMENTS

| | | |
|---|---|---|
| CN | 101558081 A | 10/2009 |
| CN | 103282502 A | 9/2013 |
| CN | 103547272 A | 1/2014 |
| CN | 104189897 A | 12/2014 |
| CN | 105658797 A | 6/2016 |
| CN | 105899666 A | 8/2016 |
| CN | 107530436 A | 1/2018 |
| CN | 108026527 A | 5/2018 |
| CN | 108271387 A | 7/2018 |
| CN | 108949772 A | 12/2018 |
| CN | 110637086 A | 12/2019 |
| CN | 111041025 A | 4/2020 |
| EP | 2652134 B1 | 3/2017 |
| EP | 2970351 B1 | 9/2017 |
| EP | 2991661 B1 | 3/2019 |
| EP | 3546579 A1 | 10/2019 |
| EP | 2971010 B1 | 6/2020 |
| JP | 2006517512 A | 7/2006 |
| JP | 2018537399 A | 12/2018 |
| WO | WO-2014160129 A2 | 10/2014 |
| WO | WO-2014160129 A3 | 12/2014 |
| WO | WO-2017212009 A1 | 12/2017 |
| WO | WO-2018104538 A1 | 6/2018 |
| WO | WO-2018140362 A1 | 8/2018 |
| WO | WO-2018168999 A1 | 9/2018 |
| WO | WO-2019063843 A1 | 4/2019 |
| WO | WO-2019077001 A1 | 4/2019 |
| WO | WO-2020056370 A9 | 5/2020 |
| WO | WO-2020093053 A1 | 5/2020 |
| WO | WO-2021030778 A1 | 2/2021 |
| WO | WO-2021121173 A1 | 6/2021 |
| WO | WO-2021139474 A1 | 7/2021 |
| WO | WO-2022000884 A1 | 1/2022 |

OTHER PUBLICATIONS

Bennett et al. Control of mucin-type O-glycosylation: a classification of the polypeptide GalNAc-transferase gene family (Glycobiology, 2012, 22:736-756) (Year: 2012).*

Baenziger et al. Galactose and N-acetylgalactosamine-specific endocytosis of glycopeptides by isolated rat hepatocytes. Cell 22:611-620 (1980).

Bai, et al. (白宁超等) Research Progress of Targeted Drug Delivery System Based on Carbohydrate Compounds (基于糖类化合物靶向药物载体的研究进展). Chemical World (化学世界). vol. 59, No. 7, May 25, 2018. pp. 393-399 (English Abstract).

Connolly et al. Binding and endocytosis of cluster glycosides by rabbit hepatocytes. Evidence for a short-circuit pathway that does not lead to degradation. J. Biol. Chem. 257:939-945 (1982).

Fumoto, et al. Methods for Evaluating the Stimuli-Responsive Delivery of Nucleic Acid and Gene Medicines. Chem Pharm Bull (Tokyo). 2017;65(7):642-648. doi: 10.1248/cpb.c17-00096.

Huang, Y. Asialoglycoprotein Receptor and Its Application in Liver-targeted Drug Delivery. Jun. 2015. Progress in Biochemistry and Biophysics 42(6):501-510. DOI:10.16476/j.pibb.2015.0028 (English Abstract).

Huang Y. Preclinical and Clinical Advances of GalNAc-Decorated Nucleic Acid Therapeutics. Mol Ther Nucleic Acids. Mar. 17, 2017;6:116-132. doi: 10.1016/j.omtn.2016.12.003. Epub Dec. 10, 2016.

International search report with written opinion dated Mar. 8, 2021 for PCT/CN2020/135203 (English Translation).

International search report with written opinion dated Mar. 17, 2021 for PCT/CN2020/136010 (English Translation).

International search report with written opinion dated Mar. 25, 2021 for PCT/CN2020/123993 (English Translation).

Janas, et al. Selection of GalNAc-conjugated siRNAs with limited off-target-driven rat hepatotoxicity. Nat Commun. Feb. 19, 2018;9(1):723. doi: 10.1038/s41467-018-02989-4.

Jung, et al. CpG oligonucleotide and α-D-mannose conjugate for efficient delivery into macrophages. Applied Biological Chemistry. Published Sep. 11, 2016. 59(5): 759-763.

Kershaw, et al. Splint ligation of RNA with T4 DNA ligase. Methods Mol Biol. 2012;941:257-269. doi: 10.1007/978-1-62703-113-4_19.

Nair et al. Multivalent N-acetylgalactosamine-conjugated siRNA localizes in hepatocytes and elicits robust RNAi-mediated gene silencing. J Am Chem Soc. 136(49):16958-16961 (2014).

Office action dated Feb. 20, 2021 for CN Application No. 201911300610.2 (English Translation).

Office action dated Mar. 11, 2021 for CN Application No. 202010027183.1 (English Translation).

Office action dated Apr. 19, 2021 for CN Application No. 201911300610.2 (English Translation).

Office action dated Aug. 18, 2021 for CN Application No. 202010027183.1 (English Translation).

Springer, et al. GalNAc-siRNA Conjugates: Leading the Way for Delivery of RNAi Therapeutics. Nucleic Acid Ther. Jun. 2018;28(3):109-118. doi: 10.1089/nat.2018.0736. Epub May 24, 2018.

Wang, et al. Optimization of the Linker Length of Mannose-Cholesterol Conjugates for Enhanced mRNA Delivery to Dendritic Cells by Liposomes. Front Pharmacol. Sep. 5, 2018;9:980. doi: 10.3389/fphar.2018.00980. eCollection 2018.

Zhao, et al. Synthesis and characterization of mannosylated oligoribonucleotides. Carbohydr Res. Nov. 2, 2009;344(16):2137-2143. doi: 10.1016/j.carres.2009.08.033. Epub Aug. 31, 2009.

Mochizuki, et al. One-pot preparation of mRNA/cDNA display by a novel and versatile puromycin-linker DNA. ACS Comb Sci. Sep. 12, 2011;13(5):478-485. doi: 10.1021/co2000295. Epub Jul. 28, 2011.

(56) References Cited

OTHER PUBLICATIONS

Office action dated Nov. 8, 2022 for U.S. Appl. No. 17/559,620.
Andries, et al. N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.
Co-pending U.S. Appl. No. 17/843,162, inventors Hu; Yong et al., filed Jun. 17, 2022.
Craig, et al. Recent preclinical and clinical advances in oligonucleotide conjugates. Expert Opin Drug Deliv. Jun. 2018;15(6):629-640. doi: 10.1080/17425247.2018.1473375. Epub May 16, 2018.
European search report and opinion dated Oct. 4, 2022 for EP Application No. 20902709.3.
Ikeda, et al. Simple solid-phase synthesis and biological properties of carbohydrate-oligonucleotide conjugates modified at the 3'-terminus. Bioconjug Chem. Sep. 15, 2010;21(9):1685-90. doi: 10.1021/bc100205v.
Javanbakht, et al. Liver-Targeted Anti-HBV Single-Stranded Oligonucleotides with Locked Nucleic Acid Potently Reduce HBV Gene Expression In Vivo. Mol Ther Nucleic Acids. Jun. 1, 2018;11:441-454. doi: 10.1016/j.omtn.2018.02.005. Epub Feb. 23, 2018.
Jayaprakash, et al. Non-nucleoside building blocks for copper-assisted and copper-free click chemistry for the efficient synthesis of RNA conjugates. Org Lett. Dec. 3, 2010;12(23):5410-3. doi: 10.1021/ol102205j. Epub Nov. 4, 2010.
Office action dated Jun. 22, 2022 for U.S. Appl. No. 17/559,620.
Office action dated Jul. 14, 2022 for U.S. Appl. No. 17/559,620.
Shin, et al. Recent Advances in RNA Therapeutics and RNA Delivery Systems Based on Nanoparticles. Adv. Therap. Nov. 2018; 1 (7): 1800065 (Year: 2018).
Van Hoecke, et al. How mRNA therapeutics are entering the monoclonal antibody field. J Transl Med. Feb. 22, 2019;17(1):54. doi: 10.1186/s12967-019-1804-8.
Zhao, et al. RNA delivery biomaterials for the treatment of genetic and rare diseases. Biomaterials. Oct. 2019;217:119291. doi: 10.1016/j.biomaterials.2019.119291. Epub Jun. 20, 2019.
European search report and opinion dated Jan. 31, 2023 for EP Application No. 20942695.6.
Irache, et al. Mannose-targeted systems for the delivery of therapeutics. Expert Opin Drug Deliv. Jun. 2008;5(6):703-724. doi: 10.1517/17425247.5.6.703.
Notice of Allowance dated Mar. 6, 2023 for U.S. Appl. No. 17/559,620.
Pichon, et al. Mannosylated and histidylated LPR technology for vaccination with tumor antigen mRNA. Methods Mol Biol. 2013;969:247-274. doi: 10.1007/978-1-62703-260-5_16.
Prieve, et al. Targeted mRNA Therapy for Ornithine Transcarbamylase Deficiency. Mol Ther. Mar. 7, 2018;26(3):801-813. doi: 10.1016/j.ymthe.2017.12.024. Epub Jan. 4, 2018.
Spinelli, et al. Glycoclusters on oligonucleotide and PNA scaffolds: synthesis and applications. Chem Soc Rev. Jun. 7, 2013;42(11):4557-4573. doi: 10.1039/c2cs35406c. Epub Dec. 19, 2012.
Yan, et al. Glycotargeting to improve cellular delivery efficiency of nucleic acids. Glycoconj J. Apr. 2007;24(2-3):107-123. doi: 10.1007/s10719-006-9023-y. Epub Feb. 1, 2007.

* cited by examiner a)

b)

c)

d)

e)

f)

g)

```
SEQUENCE LISTING

<160> NUMBER OF SEQ ID NOS: 11

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcggcggcg gcagcggcgg cggcggcagc ggcggcggcg gcagc              45

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcggcggca gcggcggcgg cagcggcggc ggcagc                        36

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcggcagcg gcggcagcgg cggcagc                                  27

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcagcggca gcggcagc                                            18

<210> SEQ ID NO 5
<211> LENGTH: 9
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 agcagcagc                                                                  9

<210> SEQ ID NO 6
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg cccacccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact ctcggcatgg acgagctgta caagaagctt     720
agccatggct ccccgccggc ggtggcggcg caggatgatg gcacgctgcc catgtcttgt     780
gcccaggaga gcgggatgga ccgtcaccct gcagcctgtg cttctgctag gatcaatgtg     840

<210> SEQ ID NO 7
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gtgagcaagg gcgaggagac cacaatgggc gtaatcaagc ccgacatgaa gatcaagctg      60
aagatggagg gcaacgtgaa tggccacgcc ttcgtgatcg agggcgaggg cgagggcaag     120
ccctacgacg gcaccaacac catcaacctg gaggtgaagg agggagcccc cctgcccttc     180
tcctacgaca ttctgaccac cgcgttcagt tacggcaaca gggccttcac caagtacccc     240
gacgacatcc ccaactactt caagcagtcc ttccccgagg gctactcttg ggagcgcacc     300
atgaccttcg aggacaaggg catcgtgaag gtgaagtccg acatctccat ggaggaggac     360
tccttcatct acgagataca cctcaagggc gagaacttcc cccccaacgg ccccgtgatg     420
cagaaggaga ccaccggctg ggacgcctcc accgagagga tgtacgtgcg cgacggcgtg     480
ctgaagggcg acgtcaagat gaagctgctg ctggagggcg cggccacca ccgcgttgac     540 ttcaagacca tctacagggc caagaaggcg gtgaagctgc ccgactatca ctttgtggac     600
```

```
caccgcatcg agatcctgaa ccacgacaag gactacaaca aggtgaccgt ttacgagatc    660
gccgtggccc gcaactccac cgacggcatg gacgagctgt acaag                    705

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa aaaaaaaaa aaaaaacc                                         29

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Asn Leu Tyr Phe Gln Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Asn Leu Tyr Phe Gln Ser
1               5

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
taatacgact cactatagg                                                  19
```

MRNA TARGETING MOLECULE COMPRISING N-ACETYLGALACTOSAMINE BINDING POLYPEPTIDE AND PREPARATION METHOD THEREFOR

The present application is a continuation application of International Application No. PCT/CN2020/136010, filed Dec. 14, 2020, which claims the priority of Chinese Patent Application No. 201911300610.2, entitled "MRNA TARGETING MOLECULE COMPRISING N-ACETYLGALACTOSAMINE BINDING POLYPEPTIDE AND PREPARATION METHOD THEREFOR", filed with the China National Intellectual Property Administration on Dec. 17, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 15, 2022, is named 60943-701_301 SL.txt and is 4,819 bytes in size.

TECHNICAL FIELD

The present invention belongs to the field of biotechnology, and in particular relates to an mRNA targeting molecule comprising an N-acetylgalactosamine binding polypeptide and a preparation method therefor.

BACKGROUND OF THE INVENTION

An asialoglycoprotein receptor (ASGPR) is an abundant hetero-oligomer endocytic receptor, mainly exists on a surface of cell membrane of liver parenchymal cells facing the sinusoid, has specificity to sugar and is an endocytic receptor specifically expressed by hepatocytes. In recent years, the use of ASGPR's high-affinity ligand N-acetylgalactosamine (GalNAc) as a targeting molecule has made breakthroughs in the liver-targeting delivery of nucleic acid drugs, such as small interfering RNAs (siRNAs). Although the receptor has been discovered for many years, the messenger RNA (mRNA) delivery system based on the receptor and its ligands has failed to achieve a breakthrough because the existing technical means cannot achieve effective coupling of mRNA and GalNAc.

At present, the delivery of mRNAs into cells can be achieved through different methods, such as electroporation, sonoporation, microinjection, or cell transfection based on macromolecular compounds, but these methods are relatively toxic to cells and have certain difficulties in clinical transformations.

SUMMARY OF THE INVENTION

In view of the above technical problems, the present invention discloses an mRNA targeting molecule comprising an N-acetylgalactosamine binding polypeptide and a preparation method therefor. Through a brand-new mRNA synthesis and modification strategy, GalNAc modification of mature mRNA molecules is realized, thereby realizing the liver-targeting delivery of mRNA drugs, which is of great significance for innovative basic research, new drug design and development.

To achieve the above objects of the invention, the present invention provides the following technical solutions:

a DNA fragment for constructing an mRNA targeting molecule comprising an N-acetylgalactosamine binding polypeptide. The DNA fragment comprises a promoter, a target gene, a specific protease cleavage sequence, and a polypeptide GlaNAc Binding Domain (GBD) sequence capable of binding to N-acetylgalactosamine, that are sequentially connected.

With this technical solution, the DNA fragment can be used to construct an mRNA targeting molecule comprising an N-acetylgalactosamine binding polypeptide.

As a further improvement of the present invention, the GBD sequence is one or a combination of more than one of SEQ ID NOs.1-5.

As a further improvement of the present invention, the target gene sequence is set forth in SEQ ID NO. 6 or 7, wherein the target gene can be replaced with other genes, and the corresponding target genes can be selected according to different diseases to be treated.

As a further improvement of the present invention, the specific protease cleavage sequence is one or more of T2A, P2A, E2A, F2A, TEV, VLP1 and SUMO specific protease cleavage sequences with a GBD sequence.

As a further improvement of the present invention, the promoter is T3, T7 or SP6 promoter.

The present invention also discloses an mRNA targeting molecule comprising an N-acetylgalactosamine binding polypeptide, which comprises an mRNA molecule obtained by in vitro transcription using a plasmid containing the above DNA fragment. The sequence of the mRNA molecule sequentially comprises a 5' cap, a target gene sequence, a specific protease cleavage sequence and a polypeptide GBD protein; the polypeptide GBD protein is obtained by ribosomal translation of the GBD sequence; and the GBD sequence end of the mRNA molecule is connected to the GBD protein through puromycin, and the GBD protein is connected to N-acetylgalactosamine through an enzymatic reaction.

With this technical solution, an mRNA molecule comprising a 5' cap, a target gene sequence, a specific protease cleavage sequence, and a GBD sequence is synthesized by in vitro transcription using the above DNA fragment as a template; under the action of T4 ligase, the mRNA molecule binds to the DNA-puromycin linker to form an mRNA-puromycin complex; through an in vitro translation system, the puromycin is connected to the tail of the antibody through the A-site of ribosome to form an mRNA-puromycin-GBD-specific protease cleavage sequence-gene function protein complex; and this product is subjected to specific protease cleavage to obtain an mRNA-puromycin-GBD complex.

Puromycin is an analog of transfer RNA (tRNA), which can bind to the A-site of ribosome during the transcription process and form a peptide bond with the polypeptide fragment being synthesized to block the elongation of the peptide fragment. In addition, puromycin can also bind to the 3' end of RNA or DNA. Based on these properties, by binding a special peptide fragment with puromycin to the 3' end of an RNA molecule, a peptide fragment-RNA fusion molecule (peptide-RNA fusion product) can be formed. In the technical solution of the present invention, based on this principle, an mRNA-peptide fragment fusion molecule is designed and synthesized, and then the coupling of the mRNA molecule and GalNAc is realized through GalNAc modification on the special peptide fragment. Under the action of N-acetylgalactosamine transferase, the N-acetylgalactosamine specifically binds to the GBD protein sequence to form an mRNA-puromycin-GBD-GalNAc complex, so that the mRNA molecule can be targeted to liver cells, thereby achieving specific delivery of mRNA drug molecules.

The present invention also discloses a method for preparing the mRNA targeting molecule comprising an N-acetylgalactosamine binding polypeptide described above, comprising the following steps:

step S1, selecting a specific cell surface receptor according to the tissue, organ or cell to which the mRNA is delivered, designing a polynucleotide sequence encoding a GBD capable of binding to N-acetylgalactosamine, and cloning a combination of a promoter sequence, a target gene sequence, a specific protease cleavage sequence, and a GBD sequence into a plasmid vector to obtain a plasmid DNA;

step S2, performing in vitro transcription using the plasmid DNA of step S1 as a template to obtain an mRNA sequence comprising a 5' cap, a target gene sequence, a specific protease cleavage sequence, and a GBD sequence;

step S3, under the action of T4 ligase, binding the mRNA molecule to the DNA-puromycin linker to form an mRNA-puromycin complex;

step S4, in vitro translating the mRNA-puromycin complex obtained in step S3, wherein the mRNA-puromycin complex is translated by a ribosome into a fusion protein sequence of gene function protein-specific protease cleavage sequence-GBD;

step S5, at the end of translation, connecting the puromycin to the tail of the antibody through the A-site of the ribosome to form an mRNA-puromycin-GBD-specific protease cleavage sequence-gene function protein complex;

step S6, cleaving the product obtained in step S5 by a specific protease, wherein the part of the specific protease cleavage sequence-gene function protein in the mRNA-puromycin-GBD-specific protease cleavage sequence-gene function protein complex is cleaved to obtain an mRNA-puromycin-GBD complex; and step S7, under the action of N-acetylgalactosamine transferase, specifically binding N-acetylgalactosamine to the GBD protein sequence to form an mRNA-puromycin-GBD-GalNAc complex.

As a further improvement of the present invention, the GBD sequence is set forth in SEQ ID NOS. 1-5.

SEQ ID No. 1
GGCGGCGGCGGCAGCGGCGGCGGCGGCAGCGGCGGCGGCGGCAGC

SEQ ID No. 2
GGCGGCGGCAGCGGCGGCGGCAGCGGCGGCGGCAGC

SEQ ID No. 3
GGCGGCAGCGGCGGCAGCGGCGGCAGC

SEQ ID No. 4
GGCAGCGGCAGCGGCAGC

SEQ ID No. 5
AGCAGCAGC

As a further improvement of the present invention, the DNA sequence of the DNA-puromycin linker is set forth in SEQ ID No. 8.

SEQ ID No. 8
AAAAAAAAAAAAAAAAAAAAAAAAAAACC

As a further improvement of the present invention, in step S1, the plasmid vector is modified from pCDNA3.1.

The present invention also discloses a use of the mRNA targeting molecule comprising an N-acetylgalactosamine binding polypeptide described above in the preparation of an mRNA drug for specific drug delivery using the mRNA tissue-specific delivery material targeting N-acetylgalactosamine, wherein N-acetylgalactosamine is connected to the 3' end, and by specifically binding to the asialoglycoprotein receptor on a surface of liver cells through the N-acetylgalactosamine, endocytosis is induced, which allows an mRNA to enter the cell for expression.

Compared with the prior art, the present invention has the following beneficial effects:

With the technical solution of the present invention, by connecting the 3' end of the mRNA drug molecule to a fragment of polypeptide sequence capable of coupling with GalNAc, and therefore connecting GalNAc to the mRNA-polypeptide complex, the GalNAc modification on the mature mRNA molecule is realized; the problem that the existing GalNAc conjugation technology can only achieve the direct coupling of GalNAc with a short fragment of RNA is solved. Further, since N-acetylgalactosamine can connect and specifically bind to specific target cells in liver cells, the efficacy of mRNA drug molecules is improved, solving the technical problem of targeted delivery of nucleic acid drugs in the drug delivery process, and achieving the purpose of tissue-specific delivery through GalNAc modification on mRNA without using physical methods and chemical transfection reagents.

DETAILED DESCRIPTION OF THE INVENTION

In order to better understand the present invention, the specific embodiments of the present invention will be further described in detail below in conjunction with the accompanying drawings.

A DNA fragment for constructing an mRNA targeting molecule comprising an N-acetylgalactosamine binding polypeptide, the DNA fragment comprises a promoter, a target gene, a specific protease cleavage sequence, and a polynucleotide sequence encoding a GBD capable of binding to N-acetylgalactosamine, that are sequentially connected.

Further, the GBD sequence is one or a combination of more than one of SEQ ID NOs.1-5.

The target gene sequence is set forth in SEQ ID NO. 6 or 7.

The specific protease cleavage sequence is one or more of T2A, P2A, E2A, F2A, TEV, VLP1 and SUMO specific protease cleavage sequences with the GBD sequence.

The promoter is T3, T7 or SP6 promoter.

Based on the DNA fragment constructed above, the present invention discloses an mRNA targeting molecule comprising an N-acetylgalactosamine binding polypeptide, which comprises an mRNA molecule obtained by in vitro transcription using a plasmid containing the above DNA fragment. The sequence of the mRNA molecule sequentially comprises a 5' cap, a target gene sequence, a specific protease cleavage sequence and a polypeptide GBD protein; the polypeptide GBD protein is obtained by ribosomal translation of the GBD sequence; and the GBD sequence end of the mRNA molecule is connected to the GBD protein through puromycin, and the GBD protein is connected to N-acetylgalactosamine through an enzymatic reaction.

Figure 1:
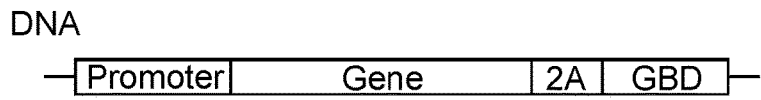
FIG. 1 is a schematic flow chart of a method for preparing the mRNA targeting molecule comprising an N-acetylgalactosamine binding polypeptide of the present invention; wherein a) is a schematic diagram of DNA fragment in a plasmid DNA; b) is a schematic diagram of an mRNA obtained by in vitro transcription using the plasmid DNA as a template and DNA-puromycin linker in a to-be-bond configuration; c) is a schematic diagram of the mRNA-puromycin complex; d) is a schematic diagram of the in vitro translation of the mRNA-puromycin complex; e) is a schematic diagram of cleavage of the mRNA-puromycin-GBD-specific protease obtained after translation to obtain an mRNA-puromycin-GBD complex; f) is a schematic diagram of the coupling of the mRNA-puromycin-GBD complex with GalNAc; and g) is a schematic diagram of the finally obtained mRNA-puromycin-GBD-GalNAc complex.
Figure 1:
Figure 1:
Figure 1:
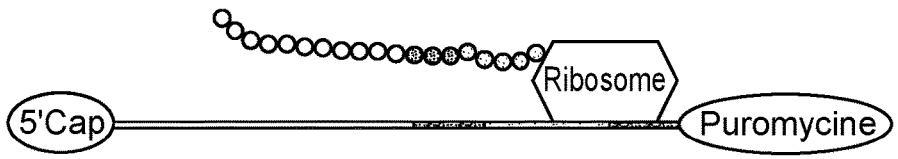
Figure 1:
Figure 1:
Figure 1:

The mRNA tissue-specific delivery material targeting N-acetylgalactosamine is prepared by the following steps:

step S1, as shown in FIG. 1, selecting a specific cell surface receptor according to the tissue, organ or cell to which the mRNA is delivered, designing a fragment of polypeptide sequence (GBD) capable of binding to N-acetylgalactosamine (GalNAc), and cloning a combination of the relevant cloning elements into a pCDNA3.1 plasmid vector;

step S2, performing in vitro transcription using the plasmid DNA of step S1 as a template, an mRNA sequence generated by the in vitro transcription comprising a 5' cap, a target gene sequence, and a specific protease cleavage sequence with a GBD sequence; and the specific protease cleavage sequence is one or more of T2A, P2A, E2A, F2A, TEV, VLP1 and SUMO;

step S3, under the action of T4 ligase, binding the mRNA molecule to a DNA-puromycin linker to form an mRNA-puromycin complex;

step S4, in vitro translating the mRNA-puromycin complex obtained in step S3, wherein the mRNA-puromycin complex is translated by a ribosome into a fusion protein sequence of gene function protein-specific protease cleavage sequence-GBD;

step S5, at the end of translation, connecting the puromycin to the tail of the antibody through the A-site of the ribosome to form an mRNA-puromycin-GBD-specific protease cleavage sequence-gene function protein complex;

step S6, cleaving the product obtained in step S5 by a specific protease, wherein under the action of 2 A peptide self-cleavage or TEV, VLP1, and SUMO specific proteases, the part of the specific protease cleavage sequence-gene function protein in the mRNA-puromycin-GBD-specific protease cleavage sequence-gene function protein complex is cleaved to obtain an mRNA-puromycin-GBD complex; and step S7, under the action of N-acetylgalactosamine transferase, specifically binding N-acetylgalactosamine to the GBD protein sequence to form an mRNA-puromycin-GBD-GalNAc complex.

Wherein, the sequence of the DNA-puromycin linker is set forth in SEQ ID NO. 8; and the GBD sequence is set forth in SEQ ID NOs. 1-5.

Further, in step S1, the plasmid vector is modified from pCDNA3.1.

Figure 2:
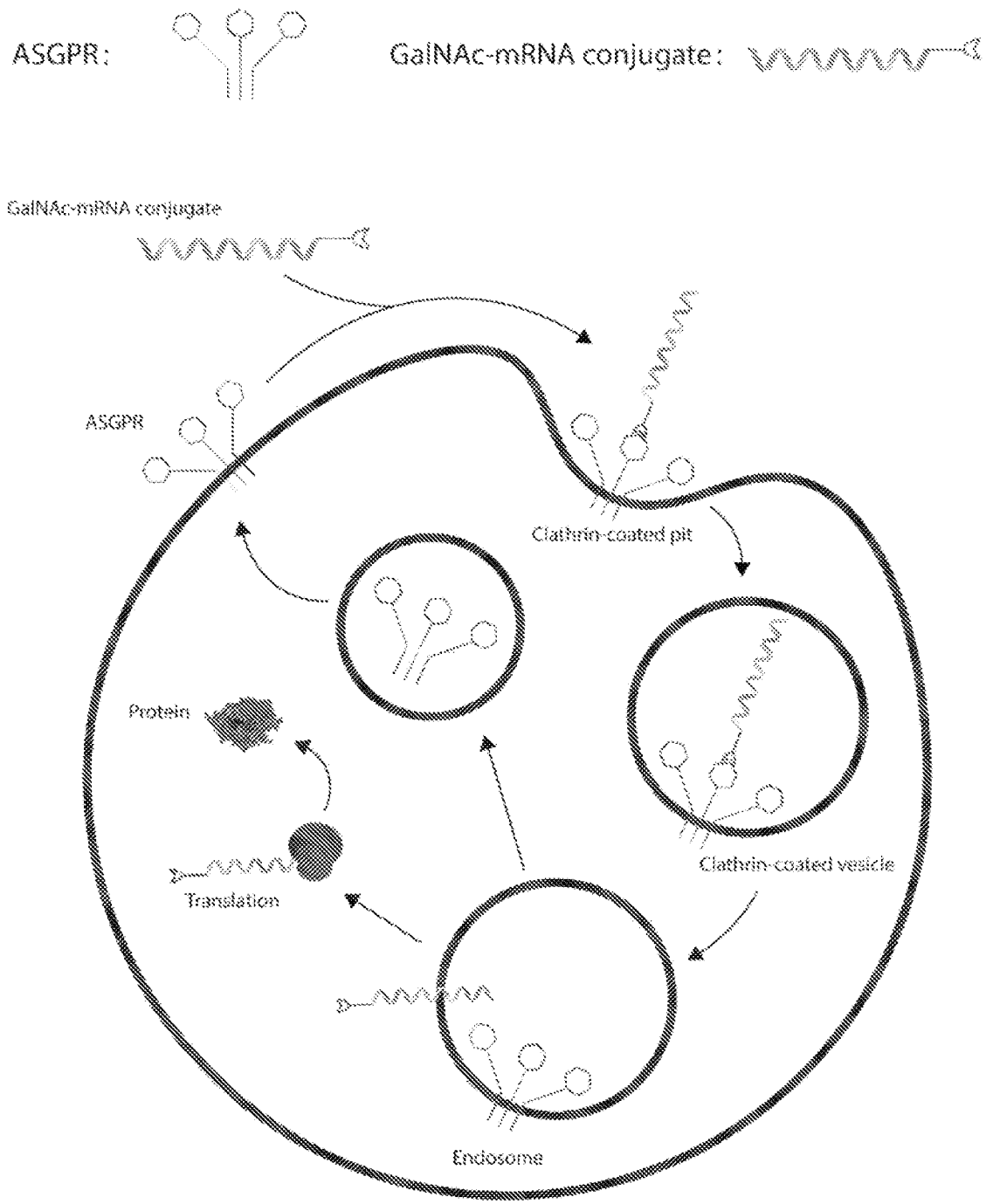
FIG. 2 is a schematic diagram of the principle of the GalNAc-mediated mRNA liver cell delivery system of the present invention, in which the GalNAc-mRNA conjugate causes endocytosis by binding to ASGPR on the liver cell surface, thereby allowing the mRNA to enter the cell.

In the preparation of an mRNA drug for specific drug delivery using the mRNA targeting molecule comprising an N-acetylgalactosamine binding polypeptide described above, a GalNAc-mediated mRNA liver cell delivery system is formed. In this system, N-acetylgalactosamine is connected to the 3' end, and by specifically binding to the asialoglycoprotein receptor on a surface of liver cells through the N-acetylgalactosamine, endocytosis is induced, which allows an mRNA to enter the cell for expression, as shown in FIG. 2.

Figure 3:
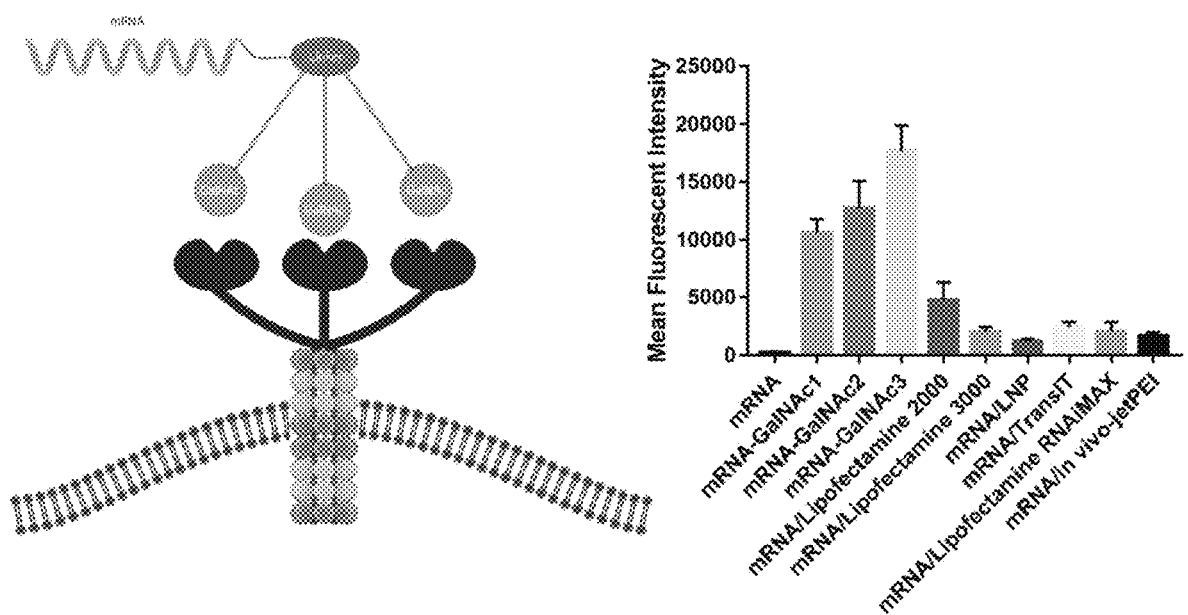
FIG. 3 is a schematic diagram of the optimization of the GalNAc-mRNA liver cell delivery system of the present invention, in which, the triple GalNAc-mRNA conjugate has the highest transfection efficiency for liver cells.

There are multiple design schemes for the GBD in the GBD-GalNAc sequence based on different designs. According to the needs, a GBD bond with only one GalNAc, a GBD bond with two GalNAcs, a GBD bond with three GalNAcs or a GBD bond with n GalNAcs can be generated. Further preferably, the use of the triple GalNAc-mRNA conjugate has the highest transfection efficiency for liver cells, and the comparison results are shown in FIG. 3.

Specific Operation Procedures:
Cell Transfection

About 24 hours after seeding 293T cells (purchased from the Cell Bank of the Chinese Academy of Sciences), the status of the cells in a 6-well plate was observed, until the confluence reached 88%-92%. In the biological safety cabinet, 90% (volume percentage) DMEM+10% (volume percentage) FBS medium was prepared. 30 minutes before transfection, the medium in the plate was discarded, and 1 mL of fresh medium, that is, 90% (volume percentage) DMEM+10% (volume percentage) FBS medium was added to each well.

Preparation of the transfection system: 200 μL opti-MEM was taken, and 10 μg of the test product (including mRNA-GalNAc1, mRNA-GalNAc2, mRNA-GalNAc3, mRNA/lipo2000, mRNA/lipo3000, mRNA/LNP, mRNA/TransIT, mRNA/lipo RNAiMAX, and mRNA/In vivo-jetPEI, at a concentration of 2 μg/μL, 5 μL) or a negative control of vector-free GFP-mRNA was added. The prepared transfection system was directly and evenly added dropwise into the cultured cells, followed by shaking well on all sides to make the transfection system evenly distributed on the cells. The medium was changed 6 hours after transfection, the old medium was aspirated, and each well was replaced with 2 mL of fresh medium (90% DMEM+10% FBS). The fluorescence intensity was measured under a fluorescence microscope 36 hours after transfection. The experimental results are shown in FIG. 3, in which the mRNA expression intensity of the mRNA-GalNAc group is significantly higher than that of other vector groups, and the triple GalNAc-mRNA conjugate achieves the highest transfection efficiency.

The present invention will be further exemplified below through specific examples, and the examples are only used to explain the present invention, instead of limiting the scope of the present invention.

Example 1

Provided herein is an mRNA targeting molecule comprising an N-acetylgalactosamine binding polypeptide, which is a novel mRNA drug capable of specific binding to liver cells. Wherein, the GalNAc modification of the mRNA molecule was bound to the GBD protein sequence of the mRNA-puromycin-GBD molecule by an N-acetylgalactosamine transferase, to form an mRNA-puromycin-GBD-GalNAc molecule. Puromycin was connected to the GBD polypeptide sequence; the mRNA molecule was obtained by in vitro transcription using a plasmid containing the above DNA fragment, the sequence of the mRNA molecule sequentially comprised a 5' cap, a target gene sequence, a specific protease cleavage sequence, and a polynucleotide sequence encoding a GBD capable of binding to N-acetylgalactosamine, and the GBD polypeptide was obtained by ribosomal translation of the GBD sequence. The mRNA targeting molecule was prepared by the following steps:

step S1, on the basis that the liver cell was the tissue to which the mRNA is delivered, selecting the green fluorescent protein mWasabi as the target gene, and designing a fragment of polypeptide sequence (GBD) capable of binding to N-acetylgalactosamine (GalNAc). The combination of the promoter sequence, the target gene sequence, the specific protease cleavage sequence, and the GBD sequence was cloned into the pCDNA3.1 plasmid vector to obtain the plasmid DNA.

In this example, the GBD sequence was one or a combination of more than one of SEQ ID NOs. 1-5.

```
                                              SEQ ID No. 1
GGCGGCGGCGGCAGCGGCGGCGGCGGCAGCGGCGGCGGCGGCAGC

SEQ ID No. 2
GGCGGCGGCAGCGGCGGCGGCAGCGGCGGCGGCAGC

SEQ ID No. 3
GGCGGCAGCGGCGGCAGCGGCGGCAGC

SEQ ID No. 4
GGCAGCGGCAGCGGCAGC

SEQ ID No. 5
AGCAGCAGC
```

In this example, the GBD as set forth in SEQ ID No. 2 was used.

The target gene sequence was set forth in SEQ ID NO. 6.

```
                                              SEQ ID No. 6
GTGAGCAAGGGCGAGGAGCTGTTCACCGGGGTGGTGCCCATC

CTGGTCGAGCTGGACGGCGACGTAAACGGCCACAAGTTCAGCGTG

TCCGGCGAGGGCGAGGGCGATGCCACCTACGGCAAGCTGACCCTG

AAGTTCATCTGCACCACCGGCAAGCTGCCCGTGCCCTGGCCCACCC

TCGTGACCACCCTGACCTACGGCGTGCAGTGCTTCAGCCGCTACCC

CGACCACATGAAGCAGCACGACTTCTTCAAGTCCGCCATGCCCGAA

GGCTACGTCCAGGAGCGCACCATCTTCTTCAAGGACGACGGCAACT

ACAAGACCCGCGCCGAGGTGAAGTTCGAGGGCGACACCCTGGTGA

ACCGCATCGAGCTGAAGGGCATCGACTTCAAGGAGGACGGCAACA

TCCTGGGGCACAAGCTGGAGTACAACTACAACAGCCACAACGTCTA

TATCATGGCCGACAAGCAGAAGAACGGCATCAAGGTGAACTTCAAG

ATCCGCCACAACATCGAGGACGGCAGCGTGCAGCTCGCCGACCACT

ACCAGCAGAACACCCCCATCGGCGACGGCCCCGTGCTGCTGCCCG
```

```
                                              -continued
ACAACCACTACCTGAGCACCCAGTCCGCCCTGAGCAAAGACCCCA

ACGAGAAGCGCGATCACATGGTCCTGCTGGAGTTCGTGACCGCCGC

CGGGATCACTCTCGGCATGGACGAGCTGTACAAGAAGCTTAGCCAT

GGCTTCCCGCCGGCGGTGGCGGCGCAGGATGATGGCACGCTGCCCA

TGTCTTGTGCCCAGGAGAGCGGGATGGACCGTCACCCTGCAGCCTG

TGCTTCTGCTAGGATCAATGTG
```

The specific protease cleavage sequence was one or more of T2A, P2A, E2A, F2A, TEV, VLP1 and SUMO specific protease cleavage sequences with a GBD sequence. In this example, the specific protease cleavage sequence used was Glu-Asn-Leu-Tyr-Phe-Gln-(Gly/Ser), as set forth in SEQ ID No. 9 and SEQ ID No. 10.

The promoter was T3, T7 or SP6 promoter. In this example, the T7 promoter was used, and the sequence was set forth in SEQ ID No. 11:

```
              SEQ ID No. 11: TAATACGACTCACTATAGG
```

The DNA sequence of the DNA-puromycin linker was set forth in SEQ ID No. 8;

```
              SEQ ID No. 8: AAAAAAAAAAAAAAAAAAAAAAAAACC
``` step S2, performing in vitro transcription using the plasmid DNA of step S1 as a template, an mRNA sequence generated by the in vitro transcription comprising a 5' cap, a gene sequence, and one or more sequences of T2A, P2A, E2A, F2A, TEV, VLP1 and SUMO specific protease cleavage sequences with a GBD sequence.

step S3, under the action of T4 ligase, binding the mRNA molecule to the DNA-puromycin linker to form an mRNA-puromycin complex;

step S4, in vitro translating the mRNA-puromycin complex obtained in step S3, wherein the mRNA-puromycin complex was translated by a ribosome into a fusion protein sequence of gene function protein-specific protease cleavage polypeptide sequence-GBD polypeptide;

step S5, at the end of translation, connecting the puromycin to the tail of the antibody through the A-site of the ribosome to form an mRNA-puromycin-GBD-specific protease cleavage sequence-gene function protein complex;

step S6, cleaving the product obtained in step S5 by a specific protease, wherein under the action of 2 A peptide self-cleavage or TEV, VLP1, and SUMO specific proteases, the part of the specific protease cleavage sequence-gene function protein in the mRNA-puromycin-GBD-specific protease cleavage sequence-gene function protein complex was cleaved to obtain an mRNA-puromycin-GBD polypeptide complex; and step S7, under the action of N-acetylgalactosamine transferase, specifically binding the N-acetylgalactosamine to the GBD protein sequence to form an mRNA-puromycin-GBD-GalNAc complex.

The mRNA-puromycin-GBD-GalNAc complex can be used to specifically bind to the ASGPR receptor on a surface of liver cells to achieve specific liver delivery of an mRNA.

Figure 4:
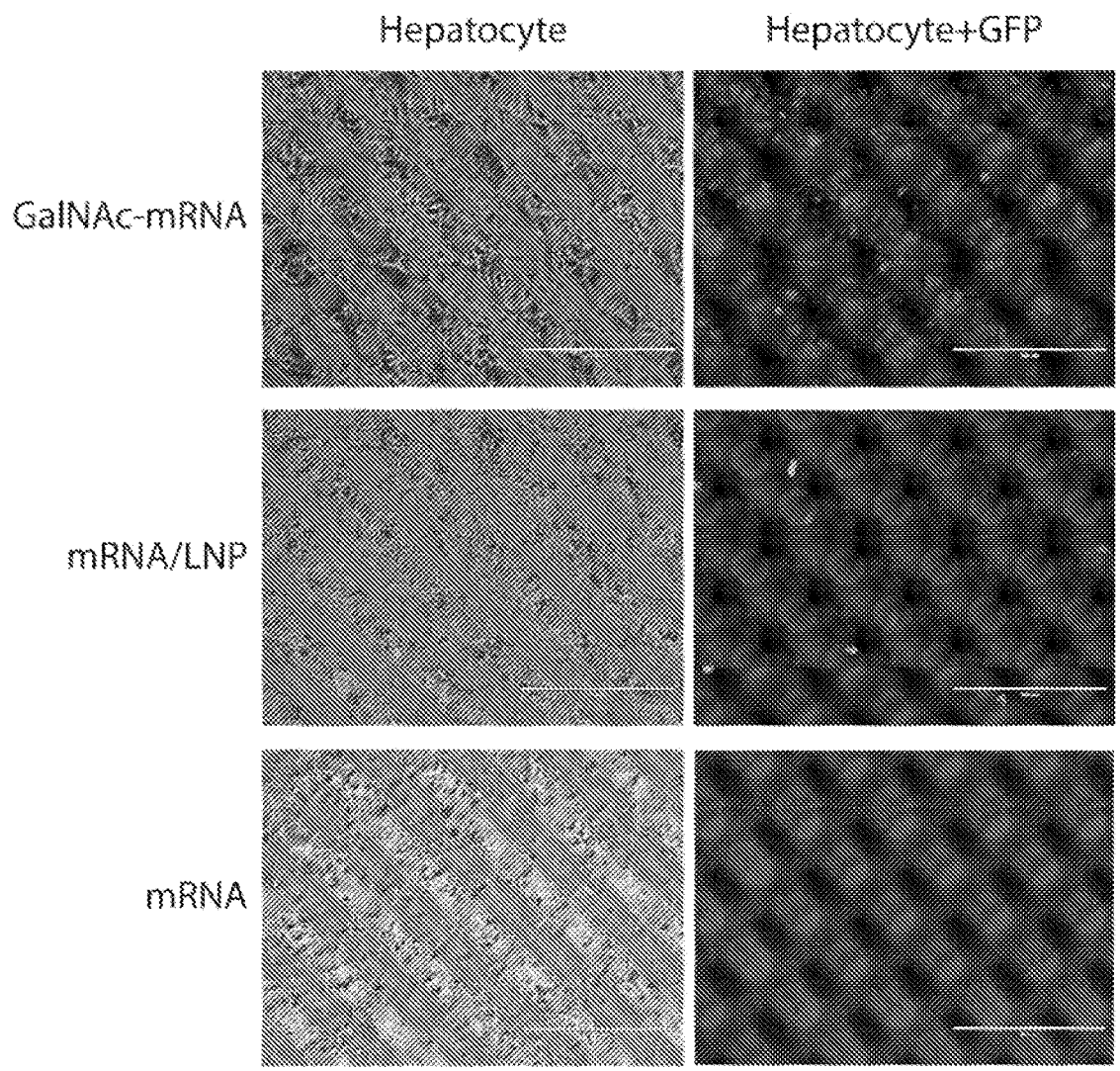
FIG. 4 is a schematic diagram of the comparison of expression of green fluorescent protein (GFP) in liver cells between the GalNAc-mRNA liver cell delivery system of the present invention and controls.

The above mRNA targeting molecule comprising an N-acetylgalactosamine binding polypeptide was used to prepare an mRNA drug for specific drug delivery. Accordingly, a GalNAc-mediated mRNA liver cell delivery system was formed, with its 3' end connected to N-acetylgalactosamine. By specifically binding to the asialoglycoprotein receptor on a surface of liver cells through the N-acetylgalactosamine, endocytosis is induced, which allows an mRNA to enter the cell for expression. Comparative experiments showed that, as shown in FIG. 4, the delivery system comprising the mRNA targeting molecule comprising an N-acetylgalactosamine binding polypeptide was more efficient in expression of green fluorescent protein (GFP) in liver cells than the existing mRNA and mRNA/LNP delivery systems.

Specific Operation Procedures:

Cell Transfection

About 24 hours after seeding 293T cells (purchased from the Cell Bank of the Chinese Academy of Sciences), the status of the cells in a 6-well plate was observed, until the confluence reached 88%-92%. In the biological safety cabinet, 90% (volume percentage) DMEM+10% (volume percentage) FBS medium was prepared. 30 minutes before transfection, the medium in the plate was discarded, and 1 mL of fresh medium, that is, 90% (volume percentage) DMEM+10% (volume percentage) FBS medium was added to each well.

Preparation of the transfection system: 200 μL opti-MEM was taken, and 10 μg of the test product (GFP mRNA-GalNAc and GFP mRNA/LNP, at a concentration of 2 μg/μL, 5 μL) or a negative control of vector-free GFP-mRNA (at a concentration of 2 μg/μL, 5 μL) was added. The prepared transfection system was directly and evenly added dropwise into the cultured cells, followed by shaking well on all sides to make the transfection system evenly distributed on the cells. The medium was changed 6 hours after transfection, the old medium was aspirated, and each well was replaced with 2 mL of fresh medium (90% DMEM+10% FBS). The fluorescence intensity was measured under a fluorescence microscope 36 hours after transfection. The experimental results were shown in FIG. 4, in which the mRNA expression intensity of the mRNA-GalNAc group is significantly higher than that of the LNP vector group.

Example 2

Provided herein is an mRNA targeting molecule comprising an N-acetylgalactosamine binding polypeptide, which was prepared by the following steps:

step S1, on the basis that the liver cell was the tissue to which the mRNA is delivered, selecting the luciferase (Luc) as the target gene, and designing a fragment of polypeptide sequence (GBD) capable of binding to N-acetylgalactosamine (GalNAc), and cloning a combination of the relevant cloning elements into the pCDNA3.1 plasmid vector, wherein, the DNA fragment in the plasmid DNA included a promoter, a target gene, a specific protease cleavage sequence, and a polynucleotide sequence encoding a GBD capable of binding to N-acetylgalactosamine, that were sequentially connected.

In this example, the GBD as set forth in SEQ ID No. 2 was used as the GBD sequence.

The target gene sequence was set forth in SEQ ID NO. 7.

```
                                          SEQ ID No. 7
GTGAGCAAGGGCGAGGAGACCACAATGGGCGTAATCAAGCCC

GACATGAAGATCAAGCTGAAGATGGAGGGCAACGTGAATGGCCAC

GCCTTCGTGATCGAGGGCGAGGGCGAGGGCAAGCCCTACGACGGC
```

```
-continued
ACCAACACCATCAACCTGGAGGTGAAGGAGGGAGCCCCCCTGCCC

TTCTCCTACGACATTCTGACCACCGCGTTCAGTTACGGCAACAGGG

CCTTCACCAAGTACCCCGACGACATCCCCAACTACTTCAAGCAGTC

CTTCCCCGAGGGCTACTCTTGGGAGCGCACCATGACCTTCGAGGAC

AAGGGCATCGTGAAGGTGAAGTCCGACATCTCCATGGAGGAGGAC

TCCTTCATCTACGAGATACACCTCAAGGGCGAGAACTTCCCCCCCA

ACGGCCCCGTGATGCAGAAGGAGACCACCGGCTGGGACGCCTCCA

CCGAGAGGATGTACGTGCGCGACGGCGTGCTGAAGGGCGACGTCA

AGATGAAGCTGCTGCTGGAGGGCGGCGGCCACCACCGCGTTGACT

TCAAGACCATCTACAGGGCCAAGAAGGCGGTGAAGCTGCCCGACTA

TCACTTTGTGGACCACCGCATCGAGATCCTGAACCACGACAAGGAC

TACAACAAGGTGACCGTTTACGAGATCGCCGTGGCCCGCAACTCCA

CCGACGGCATGGACGAGCTGTACAAG
```

In this example, the specific protease cleavage sequence used was Glu-Asn-Leu-Tyr-Phe-Gln-(Gly/Ser), as set forth in SEQ ID No. 9 and SEQ ID No. 10. The promoter was T3, T7 or SP6 promoter.

In this example, the T7 promoter was used, and the sequence was set forth in SEQ ID No. 11:

```
SEQ ID No. 11: TAATACGACTCACTATAGG
```

The DNA sequence in the DNA-puromycin linker was set forth in SEQ ID No. 8;

```
                                       SEQ ID No. 8
AAAAAAAAAAAAAAAAAAAAAAAAAACC
``` step S2, performing in vitro transcription using the plasmid DNA of step S1 as a template, an mRNA sequence generated by the in vitro transcription comprising a 5' cap, a gene sequence, and one or more sequences of T2A, P2A, E2A, F2A, TEV, VLP1 and SUMO specific protease cleavage sequences with a GBD sequence.

step S3, under the action of T4 ligase, binding the mRNA molecule to the DNA-puromycin linker to form an mRNA-puromycin complex;

step S4, in vitro translating the mRNA-puromycin complex obtained in step S3, wherein the mRNA-puromycin complex was translated by a ribosome into a fusion protein sequence of gene functional protein-specific protease cleavage sequence-GBD.

step S5, at the end of translation, connecting the puromycin to the tail of the antibody through the A-site of the ribosome to form an mRNA-puromycin-GBD-specific protease cleavage sequence-gene function protein complex.

step S6, cleaving the product obtained in step S5 by a specific protease, wherein under the action of 2 A peptide self-cleavage or TEV, VLP1, and SUMO specific proteases, the part of the specific protease cleavage sequence-gene function protein in the mRNA-puromycin-GBD-specific protease cleavage sequence-gene function protein complex was cleaved to obtain the mRNA-puromycin-GBD complex.

step S7, under the action of N-acetylgalactosamine transferase, specifically binding the N-acetylgalactosamine to the GBD protein sequence to form an mRNA-puromycin-GBD-GalNAc complex.

The above mRNA targeting molecule comprising an N-acetylgalactosamine binding polypeptide was used to prepare an mRNA drug for specific drug delivery. Accordingly, a GalNAc-mRNA delivery system was formed.

Specific Operation Procedures:

The luciferase modified Luc mRNA-GalNAc, Luc mRNA/LNP and Luc mRNA prepared in the above example were directly introduced into the systemic circulation of mice via tail vein administration, and the expression intensity of the modified mRNA in vivo was characterized via the in vivo biofluorescence signals.

Tail Vein Injection

Balb/c mice were fixed on the platform for tail vein injection, and 200 μg of the above three mRNA drugs (1 μg/m, 200 μL) were injected, respectively. Fluorescence imaging observation was performed 24 hours later.

Small Animal Imaging

D-fluorescein substrate was dissolved in a physiological saline to obtain a solution at a concentration of 15 mg/mL, and 100 μL of the solution was injected into the mice through the tail vein. 10 minutes later, the IVIS small animal imaging system was used to quantitatively analyze the signal intensity in the lung.

Figure 5:
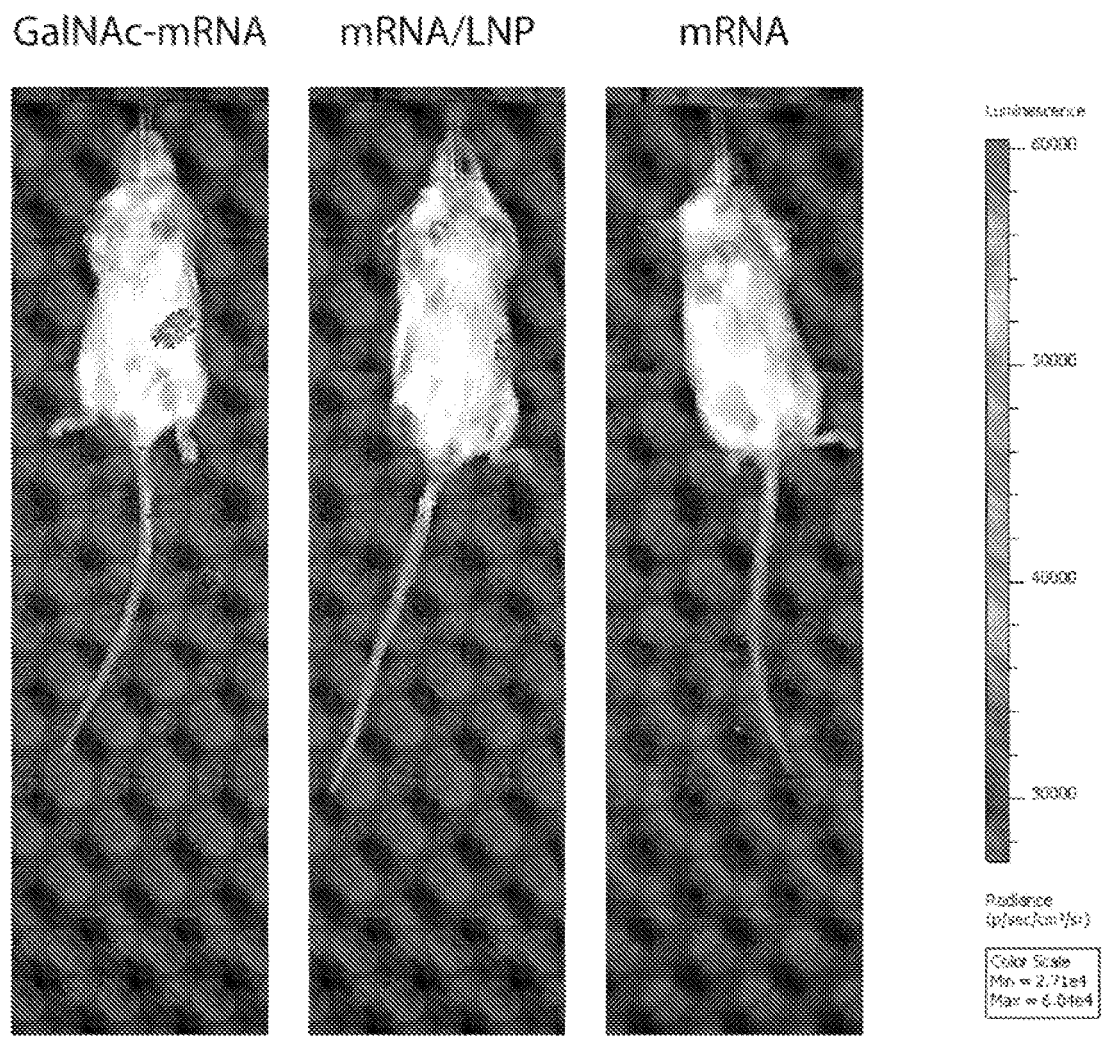
FIG. 5 is a schematic diagram of the results of delivering luciferase (Luc) to the liver tissue in vivo using the GalNAc-mRNA liver cell delivery system of the present invention and controls.

Comparative experiments showed that, as shown in FIG. 5, the GalNAc-mRNA delivery system could be more efficient in delivering luciferase (Luc) to the liver tissue than the existing mRNA and mRNA/LNP delivery systems.

The foregoing description is only the preferred embodiments of the present invention. It should be noted that for those of ordinary skill in the art, several improvements and embellishments can be made without departing from the principle of the present invention, and these improvements and embellishments are also deemed to be within the scope of protection of the present invention.

What is claimed is:

1. A molecule comprising an RNA sequence, a polypeptide of an N-acetylgalactosamine (GalNAc) binding domain (GBD), and one or more GalNAcs, wherein the polypeptide of the GBD is encoded by SEQ ID NO. 2.

2. The molecule of claim 1, wherein the molecule comprises one, two, or three GalNAc(s) bound to the polypeptide of the GBD.

3. The molecule of claim 1, wherein the molecule further comprises a RNA sequence encoding a specific protease cleavage sequence.

4. The molecule of claim of 3, wherein the specific protease cleavage sequence comprises one or more of T2A, P2A, E2A, F2A, TEV, VLP1 or SUMO specific protease cleavage sequences.

5. The molecule of claim of 4, wherein the specific protease cleavage sequence comprises a sequence of SEQ ID NO: 9 or SEQ ID NO: 10.

6. The molecule of claim 1, wherein the molecule further comprises a RNA sequence encoding the GBD.

7. The molecule of claim 1, wherein the molecule further comprises a DNA puromycin linker comprising a sequence of SEQ ID NO: 8.

8. The molecule of claim 1, wherein the molecule further comprises a puromycin.

9. A molecule comprising an RNA sequence, an RNA sequence encoding a specific protease cleavage sequence, an RNA sequence encoding a polypeptide of an N-acetylgalactosamine (GalNAc) binding domain (GBD), a DNA puromycin linker, a puromycin, the polypeptide of the GBD, and one or more GalNAcs that are sequentially connected, wherein the polypeptide of the GBD is encoded by SEQ ID NO. 2.

10. The molecule of claim 9, wherein the molecule comprises one, two, or three GalNAc(s) bound to the polypeptide of the GBD.

11. The molecule of claim of 9, wherein the specific protease cleavage sequence comprises one or more of T2A, P2A, E2A, F2A, TEV, VLP1 or SUMO specific protease cleavage sequences.

12. The molecule of claim 9, wherein the specific protease cleavage sequence comprises a sequence of SEQ ID NO: 9 or SEQ ID NO: 10.

13. The molecule of claim 9, wherein the DNA puromycin linker comprises a sequence of SEQ ID NO. 8.

14. A molecule made by a process comprising:
(a) obtaining a DNA fragment comprising a target sequence and a first polynucleotide sequence encoding a polypeptide of a N-acetylgalactosamine (GalNAc) binding domain (GBD), wherein the first polynucleotide sequence is set forth in SEQ ID NO. 2;
(b) in vitro transcribing the DNA fragment from (a), thereby obtaining a transcription product;
(c) ligating a puromycin to the transcription product from (b), thereby obtaining an RNA-puromycin complex;
(d) in vitro translating the RNA-puromycin complex from (c), thereby obtaining an RNA-puromycin-polypeptide complex; and
(e) conjugating one or more GalNAcs to the RNA-puromycin-polypeptide complex from (d) under an action of an N-acetylgalactosamine transferase.

15. The molecule of claim 14, wherein the DNA fragment in (a) further comprises a second polynucleotide sequence encoding a specific protease cleavage sequence between the target sequence and the first polynucleotide sequence.

16. The molecule of claim 15, wherein the specific protease cleavage sequence comprises one or more of T2A, P2A, E2A, F2A, TEV, VLP1 or SUMO specific protease cleavage sequences.

17. The molecule of claim 16, wherein the specific protease cleavage sequence comprises a sequence of SEQ ID NO: 9 or SEQ ID NO: 10.

18. The molecule of claim 17, wherein the DNA fragment further comprises a promoter.

19. The molecule of claim 18, wherein the promoter is T3, T7, or SP6.

20. The molecule of claim 18, wherein the promoter comprises a sequence as set forth in SEQ ID NO: 11.

21. The molecule of claim 17, wherein the DNA fragment is expressed in a plasmid vector.

22. The molecule of claim 15, wherein the process further comprises cleaving the RNA-puromycin-polypeptide complex obtained from (d).

23. The molecule of claim 14, wherein the puromycin in (c) further comprises a DNA puromycin linker comprising a sequence of SEQ ID NO. 8.

* * * * *